United States Patent [19]

Christensen

[11] Patent Number: 5,095,167

[45] Date of Patent: Mar. 10, 1992

[54] ISOPARAFFIN:OLEFIN ALKYLATION PROCESS

[75] Inventor: Gary Christensen, Sewell, N.J.

[73] Assignee: Mobil Oil Corporation, Fairfax, Va.

[21] Appl. No.: 650,362

[22] Filed: Feb. 4, 1991

[51] Int. Cl.$^5$ .......................... C07C 2/60; C07C 2/62
[52] U.S. Cl. .................... 585/720; 585/722; 585/707; 585/726; 585/727; 585/920; 585/923
[58] Field of Search ............... 585/720, 722, 726, 727, 585/707, 920, 923

[56] References Cited

U.S. PATENT DOCUMENTS

| | | | |
|---|---|---|---|
| 2,296,370 | 9/1942 | Slotterbeck | 196/10 |
| 2,296,371 | 9/1942 | Slotterbeck et al. | 196/10 |
| 2,345,095 | 3/1944 | Bruner et al. | 260/683.4 |
| 2,804,491 | 8/1957 | May et al. | 260/683.4 |
| 2,939,890 | 6/1960 | Hervert et al. | 260/671 |
| 3,131,230 | 4/1964 | Hervert et al. | 260/671 |
| 3,236,671 | 2/1966 | Dybalski et al. | 106/277 |
| 3,251,902 | 5/1966 | Garwood et al. | 260/683.64 |
| 3,435,092 | 3/1969 | Hutson, Jr. et al. | 585/720 |
| 3,450,644 | 6/1969 | Lanewala et al. | 252/416 |
| 3,467,728 | 9/1969 | Hervert | 260/683.2 |
| 3,549,557 | 12/1970 | Bolton et al. | 252/455 |
| 3,644,565 | 2/1972 | Biale | 260/683.43 |
| 3,647,916 | 3/1972 | Caesar et al. | 260/683.43 |
| 3,655,813 | 4/1972 | Kirsch et al. | 260/683.43 |
| 3,696,168 | 10/1972 | Vanderveer | 585/720 |
| 3,706,814 | 12/1972 | Kirsch et al. | 260/683.43 |
| 3,738,977 | 6/1973 | Biale | 260/94.9 DA |
| 3,800,003 | 3/1974 | Sobel | 260/683.49 |
| 3,862,258 | 1/1975 | Huang et al. | 260/683.44 |
| 3,873,634 | 3/1975 | Hoffman | 260/683.44 |
| 3,893,942 | 7/1975 | Yang | 252/411 |
| 3,917,738 | 11/1975 | Fenske et al. | 260/683.43 |
| 3,925,500 | 12/1975 | Wentzheimer | 260/683.44 |
| 3,925,502 | 12/1975 | Boney et al. | 585/922 |
| 3,977,621 | 8/1976 | Huffman | 242/75.5 |
| 4,276,439 | 6/1981 | Hutson, Jr. et al. | 585/720 |
| 4,308,414 | 12/1981 | Madgavkar et al. | 585/525 |
| 4,365,105 | 12/1982 | Morganson et al. | 585/525 |
| 4,384,161 | 5/1983 | Huang | 585/722 |
| 4,394,296 | 7/1983 | Madgavkar et al. | 252/433 |
| 4,429,177 | 1/1984 | Morganson et al. | 585/525 |
| 4,795,728 | 1/1989 | Kocal | 502/162 |

FOREIGN PATENT DOCUMENTS 424000 11/1944 Canada .
545441 5/1942 United Kingdom .
550711 1/1943 United Kingdom .

OTHER PUBLICATIONS

Madgavkar, A. M. et al., "Fixed-Bed Catalytic Process to Produce Synthetic Lubricants from Decene-1", Ind. Eng. Chem. Prod. Res. Dev., vol. 22, No. 4 (1983).
Albright, L. F. et al., "Alkylation of Isobutane with C$_4$ Olefins", 27 Ind. Eng. Chem. Res., 381-397 (1988).
Hutson, T. et al., "Phillips HF Alkylation Process for Alkylation of C$_3$, C$_4$, and C$_5$ Olefins", Handbook of Petroleum Refining Processes 23-28 (1986).
Albright, L. F., "Alkylation will be Key Process in Reformulated Gasoline Era", Oil and Gas Journal, Nov. 12 and 20 (1990).

*Primary Examiner*—Asok Pal
*Attorney, Agent, or Firm*—A. J. McKillop; C. J. Speciale; R. B. Furr, Jr.

[57] ABSTRACT

The present invention provides a process and apparatus for alkylating an isoparaffin with an olefin which decreases the required catalyst inventory while improving alkylate quality by internally admixing unreacted isoparaffin and alkylate product with the isoparaffin:olefin reactant stream in the draft tube of a decantation reaction vessel.

13 Claims, 1 Drawing Sheet

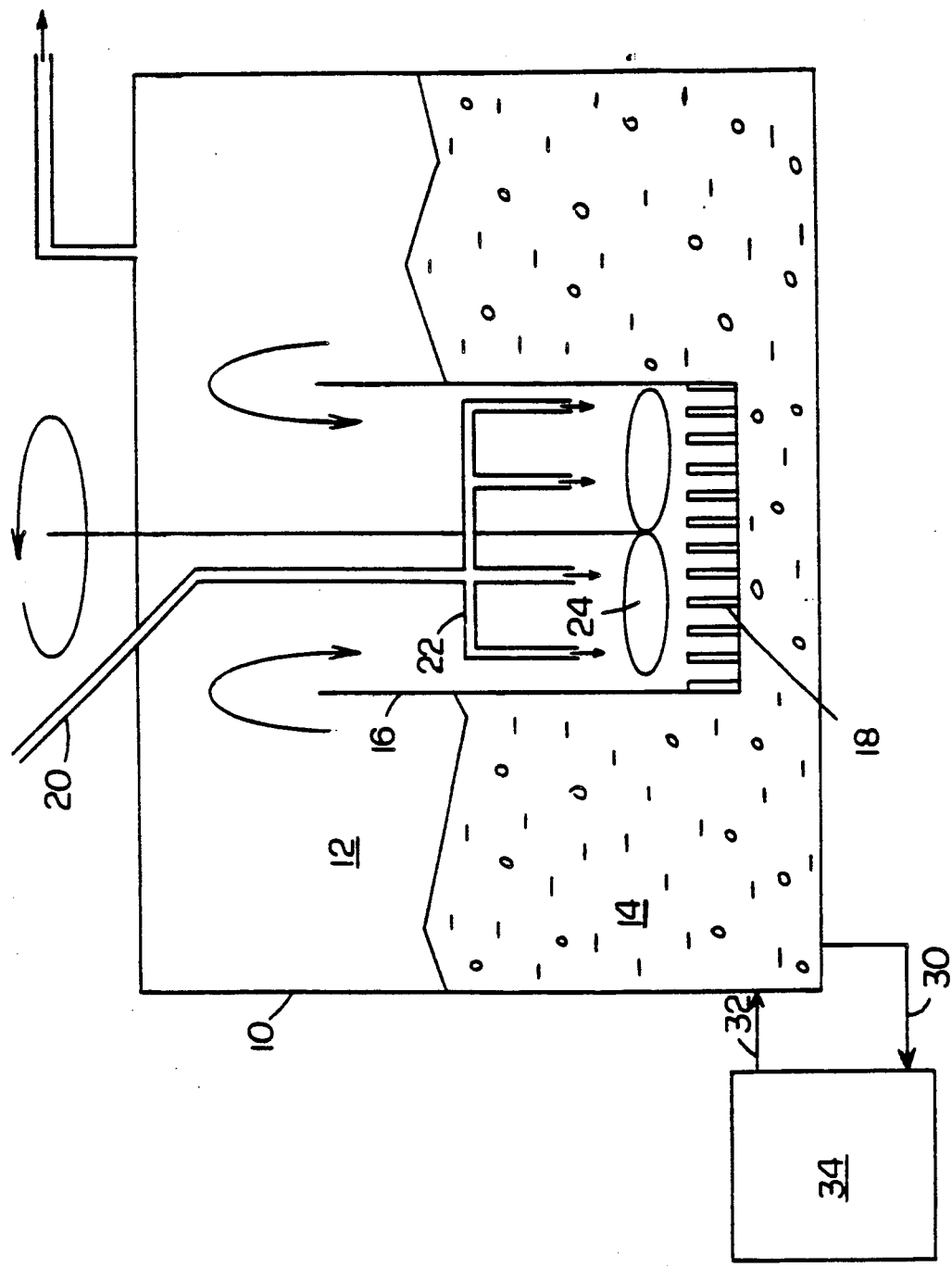

ISOPARAFFIN:OLEFIN ALKYLATION PROCESS

FIELD OF THE INVENTION

The present invention relates to the art of improving octane rating of gasoline by alkylating an isoparaffin with an olefin stream. More particularly, the invention relates to an alkylation process and apparatus which enhances contact between the hydrocarbon reactants and the alkylation catalyst while minimizing the required isoparaffin makeup and recycle rates.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

With the increasing demands for octane and the increasing environmental concerns, it has been desirable to develop an alkylation process employing safer, more environmentally acceptable catalyst systems. Specifically, it is desirable to provide an industrially viable alternative to the currently used hydrofluoric and sulfuric acid alkylation processes. Consequently, substantial efforts have been made to develop a viable isoparaffin-olefin alkylation process which avoids the environmental and safety problems associated with sulfuric and hydrofluoric acid alkylation while retaining the alkylate quality and reliability characteristic of these well-known processes. Research efforts have been directed toward solid as well as liquid alkylation catalyst systems, as reflected in the following references.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$–$C_3$ olefins using certain crystalline aluminosilicate zeolite catalysts in a fixed-, moving- or fluidized bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,236,671 discloses an alkylation reaction wherein crystalline aluminosilicate zeolites having silica to alumina mole ratios above 3 are used. The reference also discloses the use of various metals exchanged and/or impregnated on such zeolites.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkylation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio. According to the patent, problems arise in the use of solid catalyst in that they appear to age rapidly and cannot perform effectively at high olefin space velocity and the patent teaches the above solution to rectify the problem utilizing a zeolite alkylation catalyst.

The article entitled "Fixed Bed Catalytic Process to Produce Synthetic Lubricants from Decene-1", IND. ENG. CHEM. PROD. RES. DEV., Vol. 22, No. 4 (1983) teaches oligomerizing olefin to produce fluids with lubricating properties using a silica-$BF_3$-water catalyst. The authors further teach that with this system much of the $BF_3$ can be recycled to minimize $BF_3$ consumption and disposal problems. The reference teaches that water is a necessary component of the system and that in its absence a $BF_3$-silica catalyst rapidly deactivates.

In U.S. Pat. No. 4,308,414, an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 4,429,177 further relates to a method for making lubricating oil utilizing a catalyst comprising boron trifluoride, a minute amount of elemental oxygen and a particulate absorbent material such as silica.

U.S. Pat. No. 3,977,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105 also relates to oligomerizing an olefin in the presence of three-component catalyst used in making lubricating oils which comprises a particular silica absorbent with boron trifluoride and water absorbed on the silica.

U.S. Pat. No. 4,394,296 relates to a three-component catalyst used in making lubricating oils which comprises a particular silica absorbent with boron trifluoride and water absorbed on the silica.

U.S. Pat. No. 2,939,890 discloses a process for alkylating an aromatic hydrocarbon with an olefin-acting compound at alkylation conditions in the presence of an alkylation catalyst comprising boron trifluoride-modified alumina. Subsequently, U.S. Pat. No. 3,131,230 discloses the importance of the presence of small amounts of water for maintaining catalyst activity. Both of these patents are limited to aromatic alkylation processes.

U.S. Pat. No. 2,804,491 relates to an isoparaffin-olefin alkylation to make gasoline at temperatures between −20° and 150° F. utilizing a two-component catalyst comprising essentially excess $BF_3$ with a "silica stabilized gel alumina." No activators are taught.

U.S. Pat. Nos. 3,251,902 and 3,893,942, as well as French Patent 1,593,716 and the article by Kirsh and Potts, DIV. OF PET. CHEM. A.C.S. 15, A109 (1970) address alkylation in the presence of zeolite-based catalyst systems.

U.S. Pat. No. 3,467,728 relates to a process for isomerizing olefinic hydrocarbon, such as 1-butene or 1-pentene by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

Catalyst complexes comprising $BF_3$ as well as $BF_3:H_3PO_4$ adducts have been proposed, and are discussed in greater detail below. While these catalysts effectively overcome many of the safety and environmental drawbacks of sulfuric and hydrofluoric acid alkylation systems, the volume and quality of $BF_3$ alkylates have not, in the past, proven comparable to that of sulfuric or hydrofluoric acid alkylates. Further, the $BF_3$-catalyzed isobutane:butene alkylation processes typically require high isoparaffin:olefin feed ratios of at least about 5:1 to produce an alkylate gasoline product of acceptable quality.

U.K. Patent 545,441, assigned to Standard Oil Development Company, teaches a $BF_3:H_3PO_4$ catalyzed isoparaffin-olefin alkylation process.

U.S. Pat. No. 2,345,095 to Bruner teaches a paraffin-olefin alkylation process catalyzed by a boron trifluoride-water complex, represented by the formula $BF_3:nH_2O$, where n is preferably from 1 to 1.5

U.S. Pat. Nos. 2,296,370 and 2,296,371 to Slotterbeck disclose a $BF_3:H_2O:HF$ catalyst system and an isoparaffin-olefin alkylation process employing the same. The catalyst system is said to avoid yield loss due to oxidation of the resulting alkylate product.

U.K. Patent 550,711 teaches a process for increasing the activity of at least partially spent $BF_3:H_2O$ catalyst systems for reuse in an organic condensation reaction. Briefly, the process volatilizes $BF_3$ from the liquid catalyst mass to the extent required to promote separation of a distinct hydrocarbon phase from the catalyst mass. This hydrocarbon phase is then decanted off and fresh $BF_3$ is added to restore catalytic activity.

Canadian Patent 424,000 teaches a process for producing gasoline boiling range hydrocarbons from isobutane and a normally gaseous olefin by absorbing the olefin in phosphoric acid of at least 75 weight percent concentration with an amount of isobutane equal to at least three moles of isobutane per mole of alkyl phosphate in the presence of a catalytic mixture of phosphoric acid and boron halide at temperature between 20° C. and 60° C.

U.S. Pat. No. 3,873,634 to Hoffman teaches a method of increasing the rate of ethylene alkylation by isobutane by carrying out the reaction simultaneously with the alkylation of a small amount of a higher weight olefin with isobutane in the presence of a $BF_3:H_3PO_4$ catalyst complex at low temperature and pressure.

U.S. Pat. No. 3,925,500 to Wentzheimer discloses a combined acid alkylation and thermal cracking process employing a $BF_3:H_3PO_4$ acid catalyst in which unconverted propane and ethane from the alkylation process are converted, for example, to propylene and ethylene which are subsequently alkylated with isobutane to evolve a valuable liquid fuel.

U.S. Pat. No. 4,795,728 to Kocal teaches a hydrofluoric acid catalyzed alkylation process for producing motor fuel. The hydrofluoric acid catalyst complex includes from 0.5 to 5 weight percent of a cationic or anionic surfactant component enabling the process to be operated at an olefin:acid volumetric feed ratio of greater than 1.0 while maintaining acceptable alkylate quality.

Finally, the two-part article "Modern Alkylation", by Lyle F. Albright, published in the Nov. 12 and 26, 1990 issues of the *Oil and Gas Journal* summarizes the present state of $H_2SO_4$ and HF alkylation technology.

Both the liquid-catalyzed and solid-catalyzed alkylation reactions described above share certain essential features, including the need for excess isoparaffin and the criticality of effective catalyst/reactant mixing. But recycling unreacted isoparaffin at the high isoparaffin:olefin ratios required for maximum alkylate quality detracts from the economic benefit of producing the improved alkylate. Clearly, then, it would be highly desirable to provide a catalytic isoparaffin:olefin alkylation process which produces high quality alkylate at relatively low fresh feed isoparaffin:olefin ratios.

SUMMARY OF THE INVENTION

The present invention includes a process for alkylating an olefin with an isoparaffin in the presence of an alkylation catalyst comprising the steps of:

(a) providing a decantation reaction zone containing an upper hydrocarbon phase and a lower alkylation catalyst phase wherein said upper hydrocarbon phase and said lower alkylation catalyst phase are at least partially immiscible, and wherein said upper hydrocarbon phase contains both isoparaffin and alkylate;

(b) providing a longitudinally extensive draft tube traversing the interface between said upper hydrocarbon phase and said lower liquid catalyst phase;

(c) charging fresh isoparaffin and olefin feed to said longitudinally extensive draft tube at an isoparaffin:olefin molar ratio of from about 1.5:1 to about 15:1;

(d) drawing liquid from said upper hydrocarbon phase into said draft tube to admix said drawn liquid with said fresh isoparaffin and olefin feed; and (e) discharging said mixture of step (d) from a flow distributor in a lower portion of said draft tube into said lower liquid catalyst phase.

The isoparaffin:olefin molar ratio in the fresh reaction zone feed ranges from about 1.5:1 to about 15:1, and is preferably from about 2:1 to about 7:1. The ratio of recycled hydrocarbon from the upper hydrocarbon layer which is mixed with the fresh isoparaffin:olefin feed varies over a broad range, with typical ratios of recycled hydrocarbon:fresh feed of from about 5:1 to 300:1, preferably from about 15:1 to about 150:1, more preferably from about 15:1 to about 33:1, with the most preferred value depending upon the isoparaffin:olefin ratio in the fresh feed. The alkylation catalyst may suitably comprise a liquid or a solid and may optionally include a Lewis acid. If a liquid alkylation catalyst is employed, the catalyst complex preferably comprises a protic solvent and a Lewis acid.

Suitable Lewis acid constituents of the alkylation catalyst complex include boron trifluoride ($BF_3$), boron trichloride ($BCl_3$), antimony pentafluoride ($SbF_5$), and aluminum chloride ($AlCl_3$). Examples of useful protic solvents include water, hydrogen sulfide, methanol, hexanoic acid, acetic acid, trifluoroacetic acid, phosphoric acid, pyrophosphoric acid, fluorophosphoric acid, ethanesulfonic acid, benzenesulfonic acid, sulfuric acid, sulfurous acid, hydrofluoric acid, hydrochloric acid, and hydrobromic acid. Useful zeolites include, for example, ZSM-3, ZSM-4, ZSM-12, ZSM-18, ZSM-20, zeolite L, mordenite, faujasite, zeolite Y, MCM-22 and zeolite Beta. The macroreticular acid cation exchange resins useful in the alkylation catalyst complex of present invention are characterized by substantial porosity, high surface area, and a low surface acid concentration, generally less than about 0.5 milliequivalents of hydrogen ion per square meter surface area. Examples of such suitable ion exchange resins include Amberlyst-15, Amerlyst XN-1005, Amberlyst XN-1010, Amberlyst XN-1011, Amberlyst XN-1008, and Amberlite 200.

The densities of the alkylation catalyst complexes useful in the present invention facilitate rapid gravitational separation. Surprisingly, it has been found that internally mixing a portion of an upper hydrocarbon layer within the alkylation reaction zone, which layer contains a mixture of alkylated product and isoparaffin, improves both yield and alkylate quality. The result in indeed surprising as it would be reasonable to expect deterioration in product quality or yield when alkylate is charged back to the reaction zone in substantial quantities. Thus the present invention provides a process and a reactor configuration for alkylating an olefin with an isoparaffin in which the alkylation reactor effluent containing alkylation catalyst complex as well as hydrocarbons including alkylate and unreacted isoparaffin is gravitationally separated, and a portion of the less dense hydrocarbon phase is admixed with the fresh isoparaffin:olefin feed to improve olefin dilution and enhance hydrocarbon/catalyst contact.

The invention further comprises, in its apparatus aspects, an alkylation reactor comprising:

(a) a reactor vessel for retaining an upper hydrocarbon phase and a lower alkylation catalyst phase;

(b) a draft tube traversing the interface between said upper hydrocarbon phase and said lower alkylation catalyst phase;

(c) a flow distributor within said draft tube for charging fresh feedstock to said draft tube;

(d) a mixer for drawing hydrocarbon containing alkylate and isoparaffin from said upper hydrocarbon phase and admixing said hydrocarbon with fresh feedstock to form a mixed hydrocarbon charge stream; and (e) a flow distributor located in a lower portion of said draft tube for flowing finely divided droplets of said mixed hydrocarbon charge stream into said lower alkylation catalyst phase.

DESCRIPTION OF THE DRAWING

The Figure is a simplified schematic diagram showing the major processing steps of the process of the invention with reference to one embodiment of the apparatus of the invention.

DETAILED DESCRIPTION

The process of the invention converts a feedstock containing at least one isoparaffin having from 4 to 8 carbon atoms and at least one olefin having from 2 to 12 carbon atoms to a product stream containing a higher molecular weight isoparaffin. The process further includes mixing fresh isoparaffin:olefin feed, together with decanted unreacted isoparaffin and alkylate in a manner as detailed further below, and then charging the mixture to a more dense catalyst phase in a particular way to improve yield of desirable isoparaffinic alkylate while reducing the required catalyst inventory.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

Isoparaffin:olefin ratios in the reactor feed typically range from about 1.5:1 to about 15:1 to produce a high-octane isobutane:butene alkylate product at industrially useful yields. Higher isoparaffin:olefin ratios may also be used, however limited availability of produced isoparaffin within the refinery coupled with the relatively high cost of purchased isoparaffin favor isoparaffin:olefin ratios within the ranges listed above.

In the process and apparatus of the present invention alkylate product further dilutes the isoparaffin:olefin feed to the reactor as alkylate is drawn into a longitudinally extensive draft tube traversing the interface between the upper hydrocarbon layer and the lower catalyst layer. Alkylate quality, expressed as octane number, as well as alkylate yield improve with increasing dilution of isoparaffin:olefin feed with alkylate product. The extent of dilution is limited in industrial practice, however, by the volume of the reactor. In other words, relatively larger volumetric flowrates of alkylate product through the draft tube improve dilution, but on the other hand, require greater reactor volume for effective gravitational separation of the alkylate product from the alkylation catalyst.

The isoparaffin:olefin feed mixes in the draft tube with recycled hydrocarbon comprising alkylate and unreacted isoparaffin. The selected ratio of recycled hydrocarbon:fresh feed is a function of the fresh feed isoparaffin:olefin ratio and falls typically within the preferred range of 5:1 to 300:1, more preferably from 15:1 to 150:1.

Process Conditions

The present alkylation process is suitably conducted at temperatures of from about $-40°$ to about $500°$ C., preferably below about $150°$ C. to avoid undesirable side reactions. Lower reaction temperatures are preferred to maximize alkylate octane. The upper temperature limit is more critical when the process is conducted in the presence of a resin catalyst as described below. Lower temperatures are generally preferred, for example temperatures as low as $-20°$ C. may be effectively employed. Operating temperature typically falls within the range of about $-20°$ to about $60°$ C., with the most preferred operating temperatures falling within the range of about $-20°$ to about $30°$ C.

Operating pressure is controlled to maintain the reactants in the liquid phase, and is suitably from about 50 to about 1500 psig, preferably from about 100 to about 500 psig. The catalyst weight hourly space velocity as well as the Lewis acid dosage varies with the particular composite catalyst system employed.

Hydrocarbon and catalyst flow through the alkylation zone is typically controlled to provide weight hourly space velocity (WHSV) sufficient to convert about 99 percent by weight of fresh olefin to alkylate product. Typical WHSV values typically fall within the range of from about 0.01 to about 10 $hr^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

Catalysts

The alkylation catalyst complex useful in the present invention may comprise either a solid or a liquid catalyst promoted by a Lewis acid. The density of the solid and liquid catalysts useful in the present invention exceeds the density of the hydrocarbon effluent from the alkylation reaction zone to a degree sufficient for practical gravitational separation of an upper less dense hydrocarbon layer from a lower more dense catalyst layer. Typical densities for the hydrocarbon phase range from about 0.6 g/cc to about 0.8 g/cc, and are usually below about 0.7 g/cc. Densities for the alkylation catalysts, on the other hand, generally fall within the range of about 0.9 to about 2.0 g/cc.

The liquid alkylation catalysts may exhibit no more than limited miscibility with the hydrocarbon products and reactants. Specifically, the solubility of the liquid acid catalyst components in the hydrocarbon products and reactants should be less than about 3 weight percent.

Suitable solid catalyst systems include a Lewis acid with at least one selected from the group consisting of a macrorectiular ion exchange resin, a large-pore zeolite, and a nonzeolitic solid. A Lewis acid is generally considered to be a molecule which is capable of combining with another molecule or ion by forming a covalent chemical bond with two electrons from the second molecule or ion; that is, the Lewis acid is an electron acceptor. Examples of Lewis acids include boron trifluoride ($BF_3$), boron trichloride ($BCl_3$), antimony pentafluoride ($SbF_5$), and aluminum chloride ($AlCl_3$). The present invention contemplates the use of all Lewis acids as those set forth in *Friedel-Crafts and Related Reactions*, Interscience Publishers, Chapters III and IV (1963), which is incorporated herein by reference.

The non-zeolitic inorganic oxide of the solid catalyst may be selected from among the diverse inorganic oxides, examples of which include, but are not limited to, alumina, silica, boria, oxides of phorphorus, titanium dioxide, zirconium dioxide, chromia, zinc oxide, magnesia, calcium oxide, silica-alumina, silica-magnesia, silica-alumina-magnesia, silica-alumina-zirconia, as well as the naturally occurring inorganic oxides of various states of purity such as bauxite, clay, diatomaceous earth, merely to name a few. The preferred inorganic oxides are amorphous silicon dioxide and aluminum oxide. Isoparaffin/olefin alkylation in the presence of a non-zeolitic inorganic oxide and a Lewis acid is taught in U.S. Pat. No. 4,918,255 to Chou et al., as well as in U.S. Pat. No. 4,956,518 to Child et al. The entire disclosures of both are incorporated herein by reference.

The large pore crystalline molecular sieves which can be used in the present invention include those which absorb 2,2,4-trimethylpentane. Representative large pore crystalline molecular sieves include, for example, the following zeolites: ZSM-3, ZSM-4, ZSM-12, ZSM-18, ZSM-20, zeolite L, mordenite, faujasite, zeolite Y, MCM-22 and the rare earth metal-containing forms of the above-listed zeolites. Zeolite Beta can also be used in the present invention, although it is understood that zeolite Beta may exhibit characteristics of a medium-pore zeolite or a large-pore zeolite depending upon process conditions. Isoparaffin/olefin alkylation in the presence of a large pore zeolite is taught in U.S. Pat. No. 4,918,255 to Chou et al., cited above, as well as in allowed U.S. patent application Ser. No. 425,497, filed Oct. 17, 1989, which is a Continuation of Ser. No. 219,130, filed July 15, 1988, now abandoned.

Zeolite catalysts which are useful in the alkylation process of this invention include those possessing a Constraint Index of not greater than about 5 and preferably not greater than about 3. The method by which Constraint Index is determined is described fully in U.S. Pat. No. 4,016,218, incorporated herein by reference for details of the method. Constraint Index (CI) values for some typical zeolites including some which are suitable as catalysts in the aromatic alkylation process of this invention are:

| | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the aromatic aliylation process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood by those skilled in the art that the CI as utilized herein, while affording a highly useful means for characterizing the zeolites of interest, is approximate taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

Some zeolite catalysts which are useful in the process of this invention include zeolites ZSM-4, ZSM-12, ZSM-20, ZSM-35, ZSM-48, ZSM-50, MCM-22, TMA offretite, TEA mordenite, clinoptilolite, mordenite, REY and zeolite Beta. Of these, zeolites ZSM-12, MCM-22 and Beta are preferred and zeolite MCM-22 is particularly preferred.

Zeolite ZSM-4 is taught in British Patent No. 1,117,568; ZSM-12 in U.S. Pat. No. 3,832,449; ZSM-20 in U.S. Pat. No. 3,972,983; ZSM-35 in U.S. Pat. No. 4,016,245; ZSM-48 in U.S. Pat. No. 4,397,827; ZSM-50 in U.S. Pat. No. 4,640,849; and Beta in U.S. Pat. No. 3,308,069, each incorporated herein by reference.

Zeolite MCM-22, and in particular its x-ray diffraction pattern, together with a detailed description of its synthesis, are set forth in U.S. Pat. No. 4,954,325 which is incorporated by reference as if set forth at length herein.

The large pore zeolite selected for use in the present alkylation process generally exhibits an alpha value over a wide range of from less than about 1 to more than 1000. The index "Alpha value" measures zeolite acidic functionality and is described in detail in 61 *J. Catalysis* 395 (1980), which description is incorporated by reference as if set forth at length herein.

Zeolites of low acidity, i.e. zeolites having alpha values of less than about 200, can be achieved by a variety of techniques including (a) synthesizing a zeolite with a high silica:alumina ratio, (b) steaming, (c) steaming followed by dealuminization, and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g. at from about 350° to about 750° F. with pressure of from about 10 to about 200 atmospheres. Specific details of several steaming procedures are disclosed in U.S. Pat. Nos. 4,325,994; 4,374,296; and 4,418,235, which patents are incorporated as if set forth at length herein. In addition to, or apart from these steaming procedures, the surface acidity of the zeolite can be eliminated or reduced by treatment with bulky reagents as described in U.S. Pat. No. 4,520,221, which patent is incorporated herein by reference.

Additional molecular sieves which find utility in conjunction with the present invention include pillared silicates and/or clays; aluminophosphates, e.g. ALPO- 5, VPI-5; silicoaluminophosphates, e.g. SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875; and 4,742,033.

The macroreticular acid cation exchange resins useful in the present invention are characterized by substantial porosity, high surface area, and a low surface acid concentration, generally less than about 0.5 milliequivalents of hydrogen ion per square meter surface area. The cation exchange resin can contain a small amount of water, generally from about 0.5 to about 20 percent by weight. The macroreticular resins utilized in the process of this invention are characterized by the presence of acid functional groups and a structure having a high degree of true porosity while possessing rigidity and being subject to minimum volume change when immersed or removed from solvents or solutions.

The macroreticular acid cation exchange resin used is typified by the presence of sulfonic acid groups, e.g. The sulfonated styrene-divinylbenzene copolymer exchange resins such as those commercially available as Amberlyst-15, Amerlyst XN-1005, Amberlyst XN-1010, Amberlyst XN-1011, Amberlyst XN-1008, and Amberlite 200. The properties of these resins are set forth in U.S. Pat. No. 3,862,258 to Huang et al., the disclosure of which is incorporated herein by reference.

Suitable liquid catalyst complexes include a Lewis acid together with at least one protic solvent having a pKa of less than about 16. Examples of such protic solvents include water, hydrogen sulfide, methanol, hexanoic acid, acetic acid, trifluoroacetic acid, phosphoric acid, pyrophosphoric acid, fluorophosphoric acid, ethanesulfonic acid, benzenesulfonic acid, sulfuric acid, sulfurous acid, hydrofluoric acid, hydrochloric acid, and hydrobromic acid. Particularly preferred protic solvents include water and phosphoric acid.

The amount of catalyst used in the present process can be varied over relatively wide limits. In general, the amount of catalyst as measured by the weight hourly space velocity of the olefin can range from about 0.01 to about 100. The amount of catalyst selected for a particular reaction will be determined by several variables including the reactants involved as well as the nature of the catalyst and the operating conditions used.

Reactor Apparatus

Referring now to the Figure, one embodiment of the apparatus of the present invention is illustrated. Reactor vessel 10 contains two liquid phases, an upper hydrocarbon phase 12 and a lower catalyst phase 14. Draft tube 16 is located within reactor vessel 10 traversing the interface between the upper hydrocarbon phase 12 and the lower catalyst phase 14, with the upper portion of draft tube 16 opening into the upper hydrocarbon phase 12. Draft tube 16 is further equipped with a flow distributor or sparger 18 at its lower end portion, which lower portion extends downwardly into the lower catalyst phase 14.

Mixed isoparaffin:olefin feed enters the reactor vessel 10 through fresh feed inlet line 20 and fresh feed distributor 22. Rotating impeller 24 draws an internal recycle stream containing alkylate and unreacted isoparaffin from the upper hydrocarbon phase, mixes the fresh isoparaffin:olefin feed with the internal recycle stream, and forces the mixture downwardly through the sparger 18 into the catalyst phase 14.

Catalyst is continuously withdrawn from the lower catalyst phase through line 30, charged to catalyst regenerator 34, and returned to catalyst phase 14 through line 32. Catalyst regenerator 34 may comprise a catalyst treatment stage and/or fresh catalyst makeup as required by the particular alkylation catalyst employed.

Contact time between the isoparaffin:olefin reactants and the alkylation catalyst is a function of several variables, including depth of the catalyst layer, energy input to the draft tube mixing impeller, and droplet size discharged from the feedstock flow distributor into the catalyst layer. Reactor dimensions for a particular application may be determined by one of ordinary skill in the art with reference to the following discussion.

The feed distributor or sparger (designated in the Figure as 18) discharges a mixture of alkylate product, isoparaffin, and olefin into the lower catalyst layer 14, imparting to the discharged hydrocarbon mixture an initial downward velocity $v_i$. The downward path of the hydrocarbon droplets into the catalyst layer is generally limited by the lesser of the catalyst layer depth below the feed distributor, or the point of zero downward velocity, $v_o$. Hydrocarbon droplet depth at $v_o$ may be estimated by solving for depth given $v_i$ and the buoyant and frictional forces acting on the hydrocarbon droplet. Thus the contact time between a single hydrocarbon droplet and the alkylation catalyst may readily be estimated as the total time required to traverse the droplet's initial path downward through the alkylation catalyst plus the time required to float upwardly to the hydrocarbon layer.

The physical dimensions of the reactor vessel and the draft tube are generally not critical, but must meet the following minimum requirements. Reactor vessel diameter must be sufficient to prevent alkylation catalyst carryover into the draft tube due to the upward velocity of the hydrocarbon rising through the alkylation catalyst. The depth of the reactor below the level of the feed distributor (sparger) determines residence time of reactants within the alkylation catalyst phase for a given draft tube and energy input to the mixing apparatus. While the process operates effectively with any alkylation catalyst phase depth sufficient to afford the required residence time for the reactants, the safety and environmental benefits of minimizing catalyst inventory may be achieved by restricting the catalyst phase depth to the minimum depth determined for the desired residence time.

The draft tube which traverses the interface between the hydrocarbon phase and the catalyst phase extends upwardly into the catalyst phase sufficiently to avoid entraining catalyst with the hydrocarbon drawn into the top of the draft tube. Particularly, the distance between the hydrocarbon/catalyst interface and the top of the draft tube must be sufficient to avoid entrainment of catalyst due to that local velocities resulting from flow of the hydrocarbon layer into the top of the draft tube.

The draft tube may induce flow of hydrocarbon by any suitable means, such as an impeller as described above with reference to the Figure. If a blade-type mixing impeller is used, it is preferred to minimize the clearance between the outer edges of the impeller blades and the inside diameter of the draft tube for maximum efficiency. Alternatively, the draft tube may contain one or more jet ejectors or booster ejectors to induce flow from the upper hydrocarbon phase if the isoparaffin:olefin feed can be charged to the draft tube at rates sufficient to provide the necessary velocities within the ejector.

Droplet size, a key process variable, effects the extent of contact between the catalyst and the isoparaffin:olefin reactants per unit time, and the required residence time of isoparaffin:olefin reactants is proportional to droplet size. As droplet size decreases, however, the power requirement to produce the droplets increases; thus the incremental costs associated with reducing droplet size must be balanced against the benefits such as decreased catalyst inventory and reactor vessel volume.

The alkylation reaction zone effluent stream is separated into a less-dense phase enriched in hydrocarbons and a more-dense phase enriched in alkylation catalyst complex within the reaction zone. In accordance with the present invention, it has been found that these two phases may be gravitationally separated and that a portion of the hydrocarbon phase containing both alkylated product as well as unreacted isoparaffin may be used to dilute the fresh feed within the reaction zone.

While various continuous gravitational separation processes may be employed to improve the extent of separation within the reaction zone, the reactor vessel most preferably acts as a holding vessel to decant an upper, less dense, hydrocarbon layer from a lower more dense catalyst layer. Because typical densities for the hydrocarbon phase range from about 0.6 g/cc to about 0.8 g/cc, and densities for the alkylation catalysts generally fall within the range of about 0.9 to about 2.0 g/cc, the two phases are readily separable by gravitation means. Suitable gravitational separators include decanters as well as hydrocyclones. For a general discussion of gravitational separators, see 21 *Kirk-Othmer Encyclopedia of Chemical Technology* 1 (1980), which is incorporated by reference as if set forth at length herein.

Changes and modifications in the specifically described embodiments can be carried out without departing from the scope of the invention which is intended to be limited only by the scope of the appended claims.

What is claimed is:

1. A process for alkylating an olefin with an isoparaffin in the presence of an alkylation catalyst comprising the steps of:
   (a) providing a decantation reaction zone containing an upper hydrocarbon phase and a lower alkylation catalyst phase wherein said upper hydrocarbon phase and said lower alkylation catalyst phase are at least partially immiscible, and wherein said upper hydrocarbon phase contains both isoparaffin and alkylate;
   (b) providing a longitudinally extensive draft tube traversing the interface between said upper hydrocarbon phase and said lower alkylation catalyst phase;
   (c) charging fresh isoparaffin and olefin feed to said longitudinally extensive draft tube at an isoparaffin:olefin molar ratio of from about 1.5:1 to about 15:1;
   (d) drawing liquid from said upper hydrocarbon phase into said draft tube to admix said drawn liquid with said fresh isoparaffin and olefin feed; and
   (e) discharging said mixture of step (d) from a lower portion of said draft tube into said lower alkylation catalyst phase under alkylation conversion conditions to convert at least a portion of said fresh isoparaffin and olefin feed to an isoparaffins alkylate product.

2. The process of claim 1 wherein said isoparaffin:olefin molar ratio is from about 2:1 to about 7:1.

3. The process of claim 1 wherein said alkylation catalyst comprises a protic solvent and a Lewis acid.

4. The process of claim 3 wherein said protic solvent comprises at least one selected from the group consisting of water, hydrogen sulfide, methanol, hexanoic acid, acetic acid, trifluoroacetic acid, phosphoric acid, pyrophosphoric acid, fluorophosphoric acid, ethanesulfonic acid, benzenesulfonic acid, sulfuric acid, sulfurous acid, hydrofluoric acid, hydrochloric acid, and hydrobromic acid.

5. The process of claim 3 wherein said Lewis acid is selected from the group consisting of $BF_3$, $BCl_3$, $SbF_5$, and $AlCl_3$.

6. The process of claim 1 wherein said alkylation catalyst comprises a solid.

7. The process of claim 6 wherein said solid is selected from the group consisting of $Al_2O_3$ and $SiO_2$.

8. The process of claim 6 wherein said solid comprises a zeolite.

9. The process of claim 8 wherein said zeolite has a Constraint Index of less than about 5.

10. The process of claim 8 wherein said zeolite has the structure of at least one selected from the group consisting of ZSM-3, ZSM-4, ZSM-12, ZSM-18, ZSM-20, MCM-22, zeolite L, zeolite Y, and faujasite.

11. The process of claim 8 wherein said zeolite has the structure of zeolite Beta.

12. The process of claim 6 wherein said solid is selected from the group consisting of pillared silicates and clays.

13. The process of claim 6 wherein said solid is selected from the group consisting of aluminophosphates, silicoaluminophosphates and other metal aluminophosphates.

* * * * *